(12) United States Patent
Zamierowski et al.

(10) Patent No.: US 10,857,038 B2
(45) Date of Patent: Dec. 8, 2020

(54) EXTERNALLY-APPLIED PATIENT INTERFACE SYSTEM AND METHOD

(71) Applicant: KCI Licensing, Inc., San Antonio, TX (US)

(72) Inventors: David S. Zamierowski, Overland Park, KS (US); Stephen K. Bubb, St. Thomas, VI (US)

(73) Assignee: KCI Licensing, Inc., San Antonio, TX (US)

( * ) Notice: Subject to any disclaimer, the term of this patent is extended or adjusted under 35 U.S.C. 154(b) by 387 days.

(21) Appl. No.: 15/979,819

(22) Filed: May 15, 2018

(65) Prior Publication Data

US 2018/0256407 A1 Sep. 13, 2018

Related U.S. Application Data

(62) Division of application No. 14/442,388, filed as application No. PCT/US2013/069756 on Nov. 12, 2013, now Pat. No. 9,968,488.

(Continued)

(51) Int. Cl.
*A61M 1/00* (2006.01)
*A61F 13/00* (2006.01)
(Continued)

(52) U.S. Cl.
CPC ...... *A61F 13/00068* (2013.01); *A61F 13/022* (2013.01); *A61F 13/0216* (2013.01);
(Continued)

(58) Field of Classification Search
CPC ............ A61F 13/00068; A61F 13/0216; A61F 13/022; A61M 1/0088; A61M 1/009; A61M 27/00; A61M 2205/33
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 8/1982
AU 745271 12/2002
(Continued)

OTHER PUBLICATIONS

Lavery, et al., "Emerging Concepts with VAC Therapy", Podiatry Today, vol. 20, Jul. 1, 2007, 1-6.
(Continued)

*Primary Examiner* — Benjamin J Klein
(74) *Attorney, Agent, or Firm* — Law Office of Mark Brown, LLC; Mark E. Brown

(57) ABSTRACT

A surface-wound healing dressing for a wound or incision includes a slip drain located within the closed wound or incision. A wick is placed over the closed wound or incision in contact with the slip drain. A mat is placed over the wick and adapted for fluidic communication therewith. A recoil core includes a foam material and is adapted for placement on the mat. A wound healing method includes the steps of placing a slip drain, placing a wick over the slip drain, placing a recoil core over the wick and covering the recoil core with an overdrape. The overdrape is adapted for connection to an external negative pressure source, such as a vacuum.

20 Claims, 5 Drawing Sheets

Related U.S. Application Data

(60) Provisional application No. 61/725,412, filed on Nov. 12, 2012.

(51) Int. Cl.
*A61F 13/02* (2006.01)
*A61M 27/00* (2006.01)

(52) U.S. Cl.
CPC .......... *A61M 1/009* (2014.02); *A61M 1/0088* (2013.01); *A61M 27/00* (2013.01); *A61M 2205/33* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. |
| 3,115,138 A | 12/1963 | McEvenny et al. |
| 3,367,332 A | 2/1968 | Groves |
| 3,520,300 A | 7/1970 | Flower |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,981,051 A | 9/1976 | Brumlik |
| 4,080,970 A | 3/1978 | Miller |
| 4,096,853 A | 6/1978 | Weigand |
| 4,139,004 A | 2/1979 | Gonzalez |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,248,232 A | 2/1981 | Engelbrecht et al. |
| 4,250,882 A | 2/1981 | Adair |
| 4,256,109 A | 3/1981 | Nichols |
| 4,259,959 A | 4/1981 | Walker |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errade et al. |
| 4,382,441 A | 5/1983 | Svedman |
| 4,392,853 A | 7/1983 | Muto |
| 4,392,858 A | 7/1983 | George et al. |
| 4,419,093 A | 12/1983 | Deaton |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vailancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,339 A | 8/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,696,301 A | 9/1987 | Barabe |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,775,909 A | 10/1988 | Inoue |
| 4,787,888 A | 11/1988 | Fox |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,976,726 A | 12/1990 | Haverstock |
| 4,985,019 A | 1/1991 | Michelson |
| 5,007,921 A | 4/1991 | Brown |
| 5,007,936 A | 4/1991 | Woolson |
| 5,019,083 A | 5/1991 | Klapper et al. |
| 5,037,397 A | 8/1991 | Kalt et al. |
| 5,045,054 A | 9/1991 | Hood et al. |
| 5,045,075 A | 9/1991 | Ersek |
| 5,086,170 A | 2/1992 | Luheshi et al. |
| 5,092,858 A | 3/1992 | Benson et al. |
| 5,100,396 A | 3/1992 | Zamierowski |
| 5,112,338 A | 5/1992 | Anspach, III |
| 5,134,994 A | 8/1992 | Say |
| 5,139,023 A | 8/1992 | Stanley et al. |
| 5,149,331 A | 9/1992 | Ferdman et al. |
| 5,167,613 A | 12/1992 | Karami et al. |
| 5,169,399 A | 12/1992 | Ryland et al. |
| 5,176,663 A | 1/1993 | Svedman et al. |
| 5,215,522 A | 6/1993 | Page et al. |
| D337,639 S | 7/1993 | Beckman |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,291,887 A | 3/1994 | Stanley et al. |
| 5,298,015 A | 3/1994 | Komatsuzaki et al. |
| 5,318,570 A | 6/1994 | Hood et al. |
| 5,342,376 A | 8/1994 | Ruff |
| 5,344,415 A | 9/1994 | Debusk et al. |
| 5,358,494 A | 10/1994 | Svedman |
| 5,383,897 A | 1/1995 | Wholey |
| 5,423,885 A | 6/1995 | Williams |
| 5,437,622 A | 8/1995 | Carion |
| 5,437,651 A | 8/1995 | Todd et al. |
| 5,507,833 A | 4/1996 | Bohn |
| 5,522,901 A | 6/1996 | Thomas et al. |
| 5,527,293 A | 6/1996 | Zamierowski |
| D372,309 S | 7/1996 | Heldreth |
| 5,549,584 A | 8/1996 | Gross |
| 5,556,375 A | 9/1996 | Ewall |
| 5,580,353 A | 12/1996 | Mendes et al. |
| 5,584,859 A | 12/1996 | Brotz |
| 5,607,388 A | 3/1997 | Ewall |
| 5,630,819 A | 5/1997 | Ashby et al. |
| 5,636,643 A | 6/1997 | Argenta et al. |
| 5,645,081 A | 7/1997 | Argenta et al. |
| 5,716,360 A | 2/1998 | Baldwin et al. |
| 5,738,686 A | 4/1998 | Kubein-Meesenburg |
| 5,785,700 A | 7/1998 | Olson |
| 5,800,546 A | 9/1998 | Marik et al. |
| 5,827,246 A | 10/1998 | Bowen |
| 5,846,244 A | 12/1998 | Cripe |
| 5,911,222 A | 6/1999 | Lawrence et al. |
| 5,921,972 A | 7/1999 | Skow |
| 5,931,855 A | 8/1999 | Buncke |
| 5,941,859 A | 8/1999 | Lerman |
| 6,071,267 A | 6/2000 | Zamierowski |
| 6,113,618 A | 9/2000 | Nic |
| 6,126,659 A | 10/2000 | Wack |
| 6,135,116 A | 10/2000 | Vogel et al. |
| 6,142,982 A | 11/2000 | Hunt et al. |
| 6,146,423 A | 11/2000 | Cohen et al. |
| 6,159,246 A | 12/2000 | Mendes et al. |
| 6,162,907 A | 12/2000 | Habener |
| 6,174,306 B1 | 1/2001 | Fleischmann |
| 6,179,804 B1 | 1/2001 | Satterfield |
| 6,190,391 B1 | 2/2001 | Stubbs |
| 6,190,392 B1 | 2/2001 | Vandewalle et al. |

(56) References Cited

U.S. PATENT DOCUMENTS

| | | |
|---|---|---|
| 6,203,563 B1 | 3/2001 | Fernandez |
| 6,241,747 B1 | 6/2001 | Ruff |
| 6,270,517 B1 | 8/2001 | Brotz |
| RE37,358 E | 9/2001 | Del Rio et al. |
| 6,287,316 B1 | 9/2001 | Agarwal et al. |
| 6,293,929 B1 | 9/2001 | Smith et al. |
| 6,345,623 B1 | 2/2002 | Heaton et al. |
| 6,355,215 B1 | 3/2002 | Poggie et al. |
| 6,377,653 B1 | 4/2002 | Lee et al. |
| 6,398,767 B1 | 6/2002 | Fleischmann |
| 6,430,427 B1 | 8/2002 | Lee et al. |
| 6,488,643 B1 | 12/2002 | Tumey |
| 6,493,568 B1 | 12/2002 | Bell et al. |
| 6,500,209 B1 | 12/2002 | Kolb |
| 6,503,281 B1 | 1/2003 | Mallory |
| 6,540,705 B2 | 4/2003 | Norstrem et al. |
| 6,553,998 B2 | 4/2003 | Heaton et al. |
| 6,589,285 B2 | 7/2003 | Penenberg |
| 6,620,132 B1 | 9/2003 | Skow |
| 6,626,891 B2 | 9/2003 | Ohmstede |
| 6,645,226 B1 | 11/2003 | Jacobs et al. |
| 6,669,735 B1 | 12/2003 | Pelissier |
| 6,685,681 B2 | 2/2004 | Lockwood et al. |
| 6,695,823 B1 | 2/2004 | Lina et al. |
| 6,695,824 B2 | 2/2004 | Howard et al. |
| 6,726,706 B2 | 4/2004 | Dominguez |
| 6,752,794 B2 | 6/2004 | Lockwood et al. |
| 6,764,462 B2 | 7/2004 | Risk et al. |
| 6,800,074 B2 | 10/2004 | Henley et al. |
| 6,814,079 B2 | 11/2004 | Heaton et al. |
| 6,824,533 B2 | 11/2004 | Risk et al. |
| 6,828,468 B2 | 12/2004 | Ansmann et al. |
| 6,856,821 B2 | 2/2005 | Johnson |
| 6,860,903 B2 | 3/2005 | Mears et al. |
| 6,936,037 B2 | 8/2005 | Bubb |
| 6,951,553 B2 | 10/2005 | Bubb et al. |
| 6,953,480 B2 | 10/2005 | Mears et al. |
| 6,991,643 B2 | 1/2006 | Saadat |
| 7,070,584 B2 | 7/2006 | Johnson et al. |
| 7,105,021 B2 | 9/2006 | Edens et al. |
| 7,108,683 B2 | 9/2006 | Zamierowski |
| 7,381,211 B2 | 6/2008 | Zamierowski |
| 7,494,482 B2 | 2/2009 | Orgill et al. |
| 7,645,269 B2 | 1/2010 | Zamierowski |
| 7,976,519 B2 | 7/2011 | Bubb et al. |
| 8,366,693 B2 | 2/2013 | Hu et al. |
| 8,394,081 B2 | 3/2013 | Locke et al. |
| 9,456,930 B2 | 10/2016 | Zamierowski |
| 2002/0022861 A1 | 2/2002 | Jacobs et al. |
| 2002/0029063 A1 | 3/2002 | Wittman |
| 2002/0143286 A1 | 10/2002 | Tumey |
| 2004/0006319 A1 | 1/2004 | Lina et al. |
| 2005/0043818 A1 | 2/2005 | Bellon et al. |
| 2006/0079852 A1* | 4/2006 | Bubb .................. A61M 1/0027 604/317 |
| 2007/0038172 A1 | 2/2007 | Zamierowski |
| 2007/0066945 A1 | 3/2007 | Martin |
| 2008/0208171 A1 | 8/2008 | Argenta et al. |
| 2009/0012483 A1 | 1/2009 | Blott et al. |
| 2009/0227969 A1 | 9/2009 | Jaeb et al. |
| 2010/0168625 A1 | 7/2010 | Swain et al. |
| 2011/0092927 A1 | 4/2011 | Wilkes et al. |
| 2015/0157774 A1 | 6/2015 | Zamierowski |

FOREIGN PATENT DOCUMENTS

| | | |
|---|---|---|
| AU | 755496 | 12/2002 |
| CA | 2005436 | 6/1990 |
| DE | 2640413 | 3/1978 |
| DE | 4306478 | 9/1994 |
| DE | 29504378 | 9/1995 |
| EP | 0100148 | 2/1984 |
| EP | 0117632 | 9/1984 |
| EP | 0161865 | 11/1985 |
| EP | 0358302 | 3/1990 |
| EP | 1018967 | 8/2004 |
| EP | 1513478 | 12/2009 |
| GB | 692578 | 6/1953 |
| GB | 2195255 | 4/1988 |
| GB | 2197789 | 6/1988 |
| GB | 2220357 | 1/1990 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | WO9011795 | 10/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 2004060148 | 7/2004 |
| WO | 2011008360 | 1/2011 |

OTHER PUBLICATIONS

Letsou, M.D. et al., "Stimulation of Adenylate Cyclase Activity in Cultured Endothelial Cells Subjected to Cyclic Stretch", Journal of Cardiovascular Surgery, 31, 1990, 534-539.

Manwaring, et al., "Characterization of Rat Meningeal Cultures on Materials of Differing Surface Chemistry", Biomaterials, vol. 22, 2001.

Manwaring, et al., "Contact Guidance Induced Organization of Extracellular Matrix", Biomaterials, vol. 25, 2003, 3631-3638.

Masters, "Letter to the Editor", British Journal of Plastic Surgery, vol. 51(3), 1998; Elsevier Science/The British Association of Plastic Surgeons, UK, 267.

Mendez-Eastman, RN, "When Wounds Won't Heal", RN, Jan. 1998, vol. 61(1), Medical Economics Company, Inc., Montvale, NJ, USA, 20-24.

Mercier, et al., "Poly(lactide-co-glycolide) microspheres as a moldable scaffold for Cartilage Tissue Engineering", Biomaterials, vol. 26, 2005, 1945-1952.

Merriam-Webster Dictionary, "Devinigion of "furl"", http://www.merriam-webster.com/dictionary/furl as accessed on Mar. 31, 2016.

Meyer, et al., "A New Abdominal Drain for Overflowing Lavage in Instances of Severe Pancreatitis with Persistent Peritoneal Contamination", Surgery, Gynecology & Obstetrics, vol. 165, Sep. 1987.

Meyer, et al., "Selections from Bier's Hyperemic Treatment in Surgery, Medicine, and the Specialties: A Manual of Its Practical Application", W.B. Sunders Co., 2 Ed., 1909, 17-25, 44-64, 90-96, 167-170, and 210-211.

Mikos, et al., "Preparation of Poly(glycolic acid) Bonded Fiber Structures for Cell Attachment and Transplantation", Journal of Biomedical Materials Research, vol. 27, 1993, 183-189.

Miyauchi, et al., "Repair of Incisional Hernia with Prolene Hernia System", The Journal of Medical Investigation, vol. 60, p. 108-111, 2003; received for publication Aug. 8, 2002.

Morykwas, et al., "Vacuum-Assisted Closure: A new Method for Wound Control and Treatment: Animal Studies and Basic Foundation", Annals of Plastic Surgery, vol. 38, No. 6, 1997, 553-562.

Norman, et aL, "Methods for Fabrication of Nanoscale Topography for Tissue Engineering Scaffolds", Annals of Biomedical Engineering, vol. 34, No. 1, Jan. 2006, 89-101.

Orringer, et al., "Management of Wounds in Patients with Complex Enterocutaneous Fistulas", Surgery, Gynecology & Obstetrics, vol. 165, Jul. 1987, 79-80.

Pailler-Mattei, et al., "Study of Adhesion Forces and Mechanical Properties of Human Skin in vivo", J. Adhesion Sci. Technol., vol. 18, No. 15-16, 2004, 1739-1758.

Pfister, et al., "Neural Engineering to Produce In Vitro Nerve Constructs and Neurointerface", Neurosurgery: www.neurosurgery-online.com, 2007, 137-142.

(56) References Cited

OTHER PUBLICATIONS

Poritz, et al., "Percutaneous Drainge and Ileocolectomy for Spontaneus Intraabdominal Abscess in Chrohn's Disease", J. Gast. Surg., vol. 11, Jan. 19, 2007, 204-207.
Puyana, "Resuscitation of Hypovolemic Shock", Textbook of Critical Care, 5th Ed., Ch. 229, 2005, 1933-1943.
Reckard, et al., "Management of Intraabdominal Hypertension by Percutaneous Catheter Drainage", JVIR, vol. 16, No. 7, Jul. 2005, 1019-1021.
Robledo-Ogazon, et al., "Using the Vacuum Assisted Closure System VAC in the Treatment of Infected Surgical Wounds. Clinical Experience", madigraphic Artemisa, vol. 74, No. 2, Mar.-Apr. 2006, 107-113.
Sachlos, et al., "Making Tissue Engineering Scaffolds Work. Review on the Application of Solid Freeform Fabrication Technology to the Production of Tissue Engineering Scaffolds", European Cells and Materials, vol. 5, 2003, 29-40.
Safronov, "Vacuum Therapy of Trophic Ulcers of the Lower Leg with Simultaneous Autoplasty of the Skin", Ministry of Public Health of the USSR, 1967, 1-50.
Saxena, et al., "Vacuum-Assisted Closure: Microdeformations of Wounds and Cell Proliferation", Plast Reconstr Surg., 114(5), Oct. 2004, 1086-1096.
Schein, et al., "The 'sandwich technique' Management of the Open Abdomen", Br. J. Surg., vol. 73, May 1986, 369-370.
Segvich, et al., "Uniform Deposition of Protein Incorporated Mineral Layer on Three-Dimensional Porous Polymer Scaffolds", Journal of Biomedical Materials Research Part B: Applied Biomaterials 84B(2): <http://hdl.handle.net/2027.42/57926>, May 8, 2007, 340-349.
Sherck, et al., "Covering the "Open Abdomen": A Better Technique", The American Surgeon, vol. 64, Sep. 1998.
Shimko, et al., "Effect of Porosity on the Fluid Flow Characteristics and Mechanical Properties of Tantalum Scaffolds", Journal of Biomedical Materials Research, Part B, Applied Biomaterials, Sep. 24, 2004, 315-324.
Solovev, et al., "The Method of Treatment of Immature External Fistulas in the Upper Gastrointestinal Tract", S.M. Kirov Gorky State Medical Institute, 1987, 1-20.
Solovev, "Treatment and Prevention of Suture Failures After Gastric Resection", S.M. Kirov Gorky State Medical Institute, 1988, 1-55.
Stannard, et al., "Use of negative pressure wound therapy over clean, closed surgical incisions", International Wound Journal, 2012 vol. 9 (Suppl. 1), Aug. 2012, 32-39.
Svedman, "A Dressing Allowing Continuous Treatment of a Biosurface", IRCS Medical Science: Biomedical Technology; Clinical Medicine; Surgery and Transplantation, Jul. 1979, 221.
Svedman, et al., "A Dressing System Providing Fluid Supply and Suction Drainage Used for Continuous or Intermittent Irrigation", Annals of Plastic Surgery, vol. 17, No. 2, Aug. 1986, 125-133.
Svedman, "Irrigation Treatment of Leg Ulcers", The Lancet, vol. 322, Issue 8349, Sep. 3, 1983, 532-534.
Takahashi, et al., "Induction of Pluripotent Stem Cells from Mouse Embryonic and Adult Fibroblast Cultures by Defined Factors", Cell, vol. 126, Aug. 25, 2006, 663-676.
Tan, et al., "Inhibition of Osteocyte Apoptosis by Fluid Flow is Mediated by Nitric Oxide", Biochemical and Biophysical Research Communications, vol. 369, Issue 4, May 16, 2008, 1150-1154.
Tan, et al., "Osteocytes Subjected to Fluid Flow Inhibit Osteoclast Formation and Bone Resorption", Bone, vol. 4, Jul. 27, 2007, 745-751.
Tennant, "The Use of Hyperemia in the Postoperative Treatment of Lesions of the Extremities and Thorax", Jour. A.M.A., May 8, 1915, 1548-1549.
Timmenga, et al., "The Effect of Mechanical Stress on Healing Skin Wounds: An Experimental Study of Rabbits Using Tissue Expansion", British Journal of Plastic Surgery, vol. 44, 1991, 514-519.
Tribble, "An Improved Sump Drain-Irrigation Device of Simple Construction", Arch. Surg., vol. 105, Sep. 1972, 511-513.

Venturi, et al., "Mechanisms and CLinical Applications of the Vacuum-Assisted Closure (VAC) Device", Am. J. Clin. Dermatol., vol. 6 (3), 2005, 185-194.
Walsh, et al., "Directional Neurite Outgrowth Is Enhanced by Engineered Meningeal Cell-Coated Substrates", Tissue Engineering, vol. 11, No. 7/8, Mary Ann Liebert, Inc., 2005, 1085-1095.
Wilkes, et al., "3D Strain Measurement in Soft Tissue: Demonstration of a Novel Inverse Finite Element Model Algorithm on MicroCT Images of a Tissue Phantom Exposed to Negative Pressure Wound Therapy", Journal of the Mechanical Behavior of Biomedical Materials, Nov. 5, 2008, 1-16.
Yusupov, et al., "Active Wound Drainage", Vestnik Khirurgi, vol. 138, Issue 4, 1987, 42-46.
Zivadinovic, et al., "Vacuum Therapy in the Treatment of Peripheral Blood Vessels", Conference Papers of the 5th Timok Medical Days, Timok Medical Journal, Majdanpek, Copy and Certified Translation, 1986, 161-164.
Anderson, et al., "Design of Tissue Engineering Scaffolds as Delivery Devices for Mechanical and Mechanically Modulated Signals", Tissue Engineering, vol. 13, No. 10, 2007, 2525-2539.
Arcand, et al., "Negative Pressure Wound Therapy and Its Application to Orthopaedics. Part II: Clinical Application", Osteo Trauma Care, 2006, 254-258.
Argenta, et al., "Vacuum-Assisted Closure: A New Method for Wound Control and Treatment: Clinical Experience", Annals of Plastic Surgery, vol. 38, No. 6, Jun. 1997, 563-576.
Armstrong, et al., "Planter Pressure Changes Using a Novel Negative Pressure Wound Therapy Technique", Journal of the Am. Podiatric Med. Assoc., vol. 94, No. 5, Sep. 2004, 456-460.
Arnljots, et al., "Irrigation Treatment in Split-Thickness Skin Grafting of Intractable Leg Ulcers", Scand J. Plast. Reconstr. Surg., 19, Nov. 19, 1984, 211-213.
Bagautdinov, "Variant of External Aspiration in the Treatment of Purulent Diseases of Soft Tissues", Ministry of Higher and Secondary Education of the RSFSR I.N. Ulyanov Chuvash State University, 1986, 94-96.
Baig, et al., "Percutaneous Postoperative Intra-Abdominal Abscess Drainage After Elective Colorectal Surgery", Tech Coloproctol, vol. 6, 2002, 159-164.
Barker, et al., "Vacuum Pack Technique of Temporary Abdominal Closure: A 7-Year Experience with 112 Patients", The Journal Trauma: Injury, Infection and Critical Care, vol. 48, No. 2, Feb. 2000, 201-207.
Blackburn, II, MD, "Negative-Pressure Dressings as a bolster for Skin Grafts", Annals of Plastic Surgery, vol. 40, No. 5, May 1998, 453-457.
Boersma, et al., "Photogrammetric Wound Measurement with a Three-Camera Vision System", IAPRS, vol. 33, 2000.
Brabmamdam, et al., "Critical Care I", Surg. Forum Abstracts, vol. 207, No. 3S, Sep. 2008, S34-S35.
Brock, et al., "Temporary Closure of Open Abdominal Wounds: The Vacuum Pack", The Am. Surgeon,, Jan. 1995, 30-35.
Brody, et al., "Approaches to Heart Valve Tissue Engineering Scaffold Design", Journal of Biomedical Materials Research Part B: Applied Biomaterials, 2006, 16-43.
Burdette, et al., "Systemic Inflammatory Response Syndrome", eMedicine Critical Care; http://emedicine.medscape.com/article/168943-print, Apr. 16, 2007, 1-19.
Chariker, et al., "Effective Management of Incisional and Cutaneous Fistulae with Closed Suction Wound Drainage", Contemporary Surgery, vol. 34, Jun. 1989, 59-63.
Cheboksary, "Current Problems in Modern Clinical Surgery Interdepartmental Collection", Ministry of Higher and Secondary Education of the RSFSR I.N. Ulyanov Chuvash State University, May 21, 1986, 1-153.
Chinn, et al., "Closed Wound Suction Drainage", The Journal of Foot Surgery, vol. 1, No. 1, 1985, 76-81.
Culliford, et al., "A Novel Technique for Vacuum Assisted Closure Device Application in Noncontiguous Wounds", Journal of Plastic, Reconstructive and Aesthetic Surgery, 2006, 1-2.
Cunningham, "Development of in-vitro Model to Simulate Dermal Wound Bed Interaction with Granufoam and Gauze Dressing Under Sub Atmospheric Pressure", Micro CT Study-Test Cell Development, Report, Jul. 30, 2006, 1-19.

(56) References Cited

OTHER PUBLICATIONS

Dattilo, Jr., et al., "Medical Textiles: Application of an Absorbable Barbed Bi-directional Surgical Suture", Journal of Textile and Apparel, Technology and Management, vol. 2, Issue 2, Spring 2002, 1-5.

Davydov, et al., "Bacteriological and Cytological Assessment of Vacuum Therapy of Purulent Wounds", Vestnik Khirurgi, Oct. 1998, 48-52.

Davydov, et al., "Concepts for the Clinical-Biological Management of the Wound Process in the Treatment of Purulent Wounds by Means of Vacuum Therapy", Vestnik Khirurgi, Jul. 7, 1980, 132-136.

Davydov, et al., "Vacuum Therapy in the Treatment of Purulent Lactation Mastitis", Vestnik Khirurgi, May 14, 1986, 66-70.

Dee, "The Successful Management of a dehisced Surgical Wound with TNP Following Femoropopliteal Bypass", Journal of Wound Care, vol. 16, No. 1, Jan. 2007, 42-44.

Delalleau, et al., "Characterization of the Mechanical Properties of Skin by Inverse Analysis Combined with the Indentation Test", Journal of Biomechanics, vol. 39, 2006, 1603-1610.

Diridollou, et al., "In vivo Model of the Mechanical Properties of the Human Skin Under Suction", Skin Research and Technology, vol. 6, 2000, 214-221.

Dubick, et al., "Issues of Concern Regarding the Use of Hypertonic/Hyperoncotic Fluid Resuscitation of Hemorrahagic Hypotension", Shock, vol. 25, No. 4, 2006, 321-328.

Egnell Minor, "Addition to the User's Manual Concerning Overflow Protection", Industrigaton2, 461, 37 Trollhattan, Feb. 3, 1983, 2.

Egnell Minor, "Egnell Minor Instruction Book, 1st Edition, 300 7502", Feb. 1975, 1-24.

Fong, et al., "Initial Clinical Experience Using a Novel Ultraportable Negative Pressure Wound Therapy Device", Wounds, a Compendium of Clinical Research and Practice, vol. 22 Issue 9., Sep. 2010, 230-236.

Garner, et al., "Vacuum-Assisted Wound Closure Provides Early Fascial Reapproximation in Trauma Patients with Open Abdomens", The Am. Journ. Surg, vol. 182, 2001, 630-638.

Gemmiti, et al., "Fluid Flow Increases Type II Collagen Deposition and Tensile Mechanical Properties in Bioreactor-Grown Tissue-Engineered Cartilage", Tissue Engineering, vol. 12, No. 3, 2006, 469-479.

Grauhan, et al., "Prevention of Poststernotomy Wound Infections in Obese Patients by Negative Pressure Wound Therapy", The Journal of Thoracic and Cardiovascular Surgery, vol. 145, No. 5., May 2013, pp. 1387-1392.

Greer, et al., "The Use of Subatmospheric Pressure Dressing Therapy to Close Lymphocutaneous Fistulas of the Groin", British Journal of Plastic Surgery (2000), 53, 484-487.

Gupta, et al., "Guidelines for Managing Pressure Ulcers with Negative Pressure Wound Therapy", Supplement to Advances in Skin and Wound Care, vol. 17, Supp. 2, Nov. 2004, 1-16.

Herte, et al., "Comparative Wound Healing in Animal Subjects Using the Cuba System VS Conventional Surgical Instruments", The American Society of Plastic and Reconstructive Surgeons, Nov. 1978, 1-19.

Jeschke, et al., "Development of New Reconstructive Techniques: Use of Integra in Combination with Fibrin Glue and Negative-Pressure Therapy fro Reconstruction of Acute and Chronic Wounds", Departments of General Surgery and Trauma and Reconstructive Surgery, University of Regensburg, Jan. 15, 2003, 525-530.

Jeter, et al., "Managing Draining Wounds and Fistulae: New and Established Methods", Chronic Wound Care: Health Management Publications, 1990, 240-246.

Johnson, "An Improved Technique for Skin Graft Placement Using a Suction Drain", Surgery, Gynecology & Obstetrics, vol. 159, Dec. 1984, 585-586.

Kaplan, et al., "Guidelines for the Management of the Open Abdomen", Supplement to WOUNDS, Oct. 2005, 1-26.

Khatyr, "Model of the Viscoelastic Behaviour of Skin in vivo and Study of Anisotropy", Skin Research and Technology, vol. 10, 2004, 96-103.

Kostyuchenok, et al., "Vacuum Treatment in the Surgical Management of Purulent Wounds", Vestnik Khirugi, Sep. 1986, 18-21.

Kuznetsov, et al., "Vacuum and Vacuum-Sorption Treatment of open Septic Wounds, Appendix B", II All-Union conference on Wounds and Wound Infections: Presentation Abstracts Moscow, U.S.S.R., Oct. 29, 1986, 91-92.

Kwan, et al., "A Structural Model to Describe the Nonlinear stress-Strain Behavior for Parallel-Fibered Collagenous Tissues", Journal of Biomechanical Engineering, vol. 111, Nov. 1989, 361-363.

Lago, et al., "Neurobiological Assessment of Regenerative Electrodes for Bidirectional Interfacing Injured Peripheral Nerves", IEEE Transactions on Biomedical Engineering, vol. 54, No. 6, Jun. 2007, 1129-1137.

Laskin, "Minimally Invasive Total Knee Replacement Using a Mini-Mid Vastus Incision Technique and Results", Surgical Technology International, vol. 13, 2004, 231-238.

Latenser, et al., "A Pilot Study Comparing Percutaneous Decompression with Decompressive Laparotomy for Acute Abdominal Compartment Syndrome in Thermal Injury", Journal of Burn Care & Rehab., vol. 23, No. 3, May/Jun. 2002, 190-195.

"Algorithm for Abdominal Wall Construction", Plastic and Reconstructive Surgery, Jan. 2000, 207-209.

"All Silicone Jackson Pratt Style Flat Drain", C. Daniel Medical, Inc., retrieved from internet Mar. 15, 2007, http://www.cdanielmedical.com/flat-drain.html, 1-2.

"All Silicone Jackson Pratt Style Round Drain", C. Daniel Medical, Inc., retrieved from internet Mar. 15, 2007, http://www.cdanielmedical.com/round-drain.html, 1-2.

"Antibacterial Silver Wound Dressing, Bandage, Gauze and Adhesive Strips", Silverlon Woundcare Products; http://www.silverlon.com/wound.htm; retrieved from Internet Jul. 27, 2006, 1-5.

"Extended European Search Report", European Patent Application No. 14763938.9, dated Mar. 24, 2016, pp. 1-7.

"Hydrophobic Rigid Canisters", http://www.bemishealthcare.com/docs/anisterHydrophobic; Retrieved from Internet Mar. 15, 2007, 1-1.

"International Preliminary Examination Report and Search Report", PCT/GB96/02802, dated Jan. 15, 1998 and Apr. 29, 1997.

"International Search Report", PCT/GB98/02713, dated Jan. 8, 1999.

"International Search Report", PCT/GB95/01983, dated Nov. 23, 1995.

"International Search Report and Written Opinion", PCT/US2013/069756, dated Jan. 30, 2014, 1-10.

"International Search Report and Written Opinion", PCT/US2014/030860, dated Sep. 8, 2014, pp. 1-12.

"NPD 1000 Negative Pressure Wound Therapy System", Kalypto Medical: www.kalyptomedical.com, Sep. 2008, 1-4.

"Occlude", Merriam Webster Online Dictionary; http://www.merriam-webster.com/dictionary/occlude; retrieved from Internet Mar. 4, 2008.

"Patentee's Observations on the Oppositions", KCI Licensing, Inc. Response to Opponents Smith & Nephew, Inc., and Paul Hartmann Aktiengesellschaft Oppositions, Apr. 21, 2011, 1-15.

"PCT Written Opinion", PCT/GB98/02713, dated Jun. 8, 1999.

"PCT Written Opinion", PCT/GB96/028202, dated Sep. 3, 1997.

"Search Report and Written Opinion of the International Search Authority", International Application No. PCT/US06/38855 filed Oct. 3, 2006, report dated Aug. 8, 2007.

"Smith & Nephew, Inc. Opposition against EP 1,513,478", Sep. 16, 2010.

"V.A.C. Therapy Clinical Guidelines: A Reference Source for Clinicians", KCI: The Clinical Advantage, Jul. 2007, 1-92, 28.

Aktiengesellschaft, "Opposition to EP1513478", Sep. 16, 2010.

Ambrosio, et al., "V.A.C. GranuFoam Silver Dressing A New Antimicrobial Silver Foam Dressing Specifically Engineered for Use with V.A.C. Therapy", http://silverlon.com/fda.html, retrieved from the Internet Jul. 27, 2006, 1-71.

\* cited by examiner

EXTERNALLY-APPLIED PATIENT INTERFACE SYSTEM AND METHOD

CROSS-REFERENCE TO RELATED APPLICATIONS

This application is a Divisional of U.S. Non-Provisional patent application Ser. No. 14/442,388, filed Nov. 12, 2013, which claims priority in International Application No. PCT/US2013/069756, filed Nov. 12, 2013, which claims priority in U.S. Provisional Patent Application No. 61/725,412, filed Nov. 12, 2012, both of which are incorporated herein by reference.

The following patents are incorporated herein by reference: U.S. Pat. No. 6,951,553, issued on Oct. 4, 2005; U.S. Pat. No. 6,936,037, issued on Aug. 30, 2005; U.S. Pat. No. 7,976,519, issued on Jul. 12, 2011; and U.S. Pat. No. 8,956,335, issued on Feb. 17, 2015.

BACKGROUND OF THE INVENTION

1. Field of the Invention

The present invention relates generally to externally-applied wound dressings and wound closure methods.

2. Description of the Related Art

Wound-dressing and wound-healing include what is known as "moist wound healing." Three major components that constitute the external and physical environment of the healing wound should, in an ideal wound-healing environment, be controlled. First, wound healing is inversely related to bacterial growth. Second, it has been shown that, holding other variables constant, there is a clear linear relationship between the moisture level at the wound-site and the rate of epithelial advancement. The final important characteristic is the surface contact property of the wound dressing. The surface contact property can help to control the other two major factors. The contact layer must be made of a suitable material that promotes endurance of the dressing as well as comfort to the patient.

Thin pieces of foam have been used in moist-wound healing applications. The external face of the thin foam was more open allowing for enough moisture retention initially, but then allowing drying to occur with the dressing still in place. The internal face (or tissue-contact face) had a compressed or less-open pore configuration. Because this foam did not adhere to the wound, it could be moved or removed without disrupting the epithelium. However, this practice was often limited to small incisions since the thin foam is incapable of managing a large amount of exudate from a large, fresh wound, and if exudate accumulates under the foam piece the foam will lose surface contact, which allows bacteria to build up. By preventing granulation ingrowth, the compressed surface allows epithelial migration to advance beneath the foam. However, this type of surface had even more problems staying in intimate contact with the surface, especially in the face of exudate.

In general, epithelium advances or migrates best if moisture is maximized and then matures best if moisture is minimized. Although the idea of moist wound healing is not new, the perfection and maximization of the use of this healing process is far from perfected.

Another important aspect of wound healing relates to the respective roles of the vascular and lymphatic circulatory systems, both of which are involved in wound healing, but perform different functions. An injury to tissue involves both vascular and lymphatic circulation. The vascular system clots due to the serum and platelets, which control bleeding. Lymph fluid, however, lacks comparable coagulating properties. Moreover, the smaller-channeled peripheral lymphatic system lacks the muscled walls of the vascular circulatory system or the more proximal large-channel lymphatics. Stemming the outpouring of lymph fluid from these smaller channels involves compressing the lymphatic circulatory system through surrounding tissue swelling from an accumulation of edema and interstitial fluid. Unlike the quick response of coagulating blood, lymphatic circulatory system closure tends to be slower and can take days.

Based on the involvement of the vascular and lymphatic circulatory systems in wound healing, influencing the performance of these circulatory systems can significantly improve wound healing. Wound closure can be achieved more quickly and infection risks can be reduced by controlling the factors affecting vascular and lymphatic circulation. For example, increased perfusion of blood flow in the wound site generally promotes healing and re-epithelialization. Individual cells are also responsive to mechano-inductive forces, such as compression and tension. Properly applied and sequenced, compression and tension can promote healing.

The present invention addresses these wound healing factors by controlling and directing compression, tension and other physiological variables associated with the tissues and the fluids associated with the wound site and otherwise involved in the wound healing process.

SUMMARY OF THE INVENTION

In the embodiments of the invention described in more detail below, the unique dressing and method accomplish the objectives of enhancement and protection of (re)epithelialization, both migration and maturation, without disruption of the fragile layer by undue adherence or by motion/friction/abrasion and yet maintaining the closest of surface contacts without intervening dead space or its consequence of fluid accumulation, lytic bleeding, and micro abscess formation and lack ultimately of the ability to dry and mature epithelium. This is done by drawing away air and liquid from the wound and by introducing fresh air and/or fresh liquid to the wound to expedite healing. In this embodiment, air and moisture levels at the wound-site can be balanced by using vacuum pumps to remove excess air or moisture, and input pumps can be used to add additional dry air or moisture, or a gas or other elements which enhance healing. The vacuum pump will also provide the necessary vacuum press effect, keeping the dressing against the wound in intimate contact and enhancing healing.

DETAILED DESCRIPTION OF THE PREFERRED EMBODIMENTS

I. Preferred Embodiment External Dressing System 1102

Figure 1:
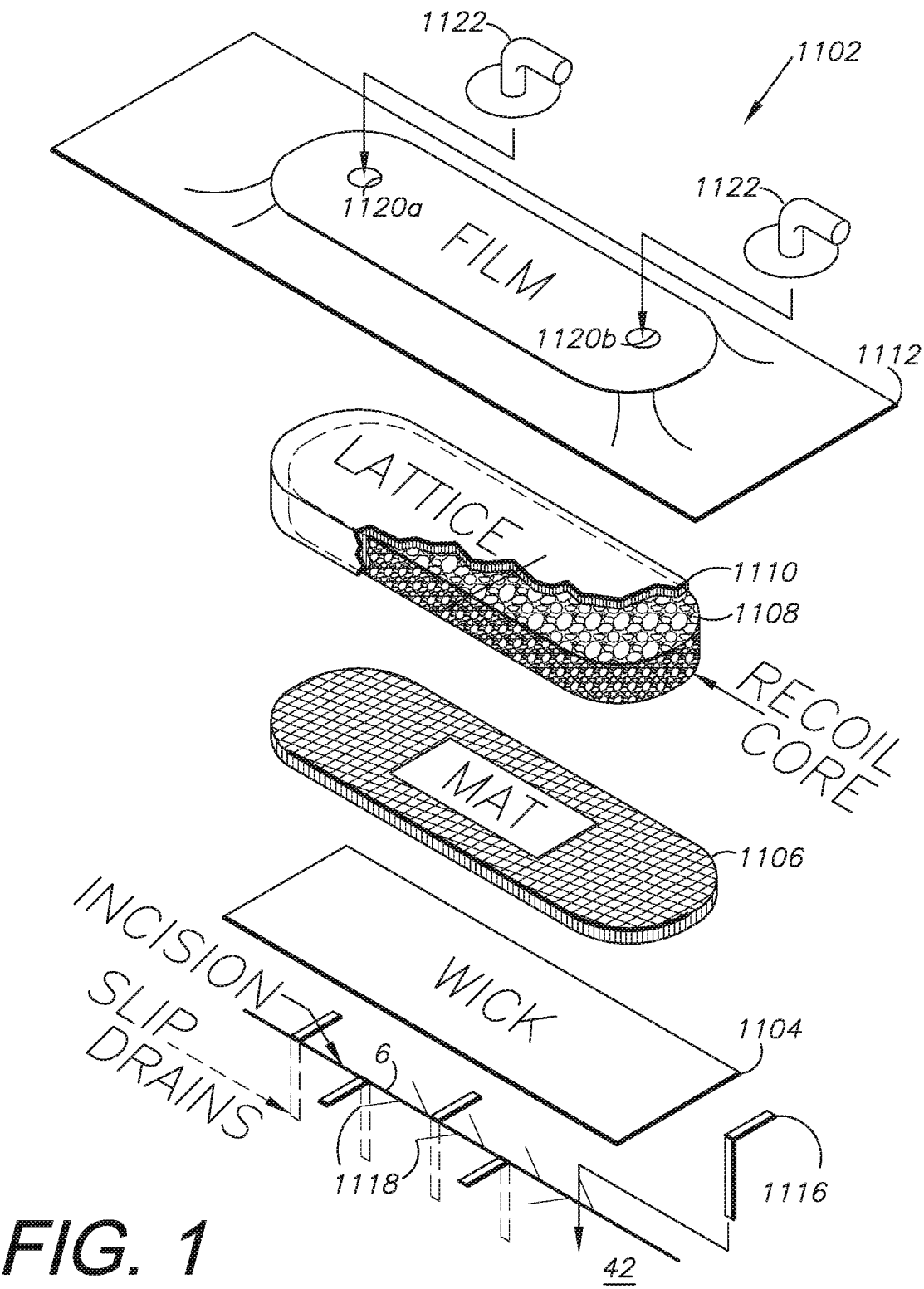
FIG. 1 is an exploded view of an external dressing system embodying an aspect of the present invention.

FIG. 1 shows the preferred embodiment external wound dressing system. A wound 6, such as an incision, can be prepared by placing an external dressing 1102 onto the wound. The dressing 1102 promotes healing at three levels of the wound repair continuum: healing (epithelialization) of an open wound, stability of a recently epithelized, but not matured, wound, and maintenance of a mature or intact epithelium without breakdown under a dressing. This dressing device 1102 has the unique advantage that it can be applied for a short period of time (days) or left in place without changing for up to six weeks. This is possible because the wound removes old air and liquid from the wound-site and introduces fresh air and liquid to the wound-site to expedite the healing process.

The external dressing 1102 can be configured with various components, which can be selected and configured for expediting and optimizing the healing procedure for various closed wounds and patient conditions. By way of non-limiting example, the external dressing 1102 includes a surface contact layer or wick 1104 comprising a wicking material layer, a mat 1106, a polyurethane foam core 1108 with a lattice covering 1110 and a semi-permeable film cover 1112 overlying the other components.

An optional, perforated tubular deep drain (not shown) can be placed in or in proximity to the wound 6 and slip drains 1116 can optionally be placed in the wound 6. Suitable, optional closures for the wound 6 include sutures 1118, staples, adhesives, etc.

Alternatively, a suitable direct-contact foam core 1108 can be placed directly on the skin surface 42 and simply covered with the membrane film cover 1112. Still further, the foam core 1108 can be completely enclosed in a cover layer of a suitable material, such as a wicking material layer. Further still, the dressing 1102 can be completely unitary and self-contained for direct placement, whereupon the pressure differential feature described below can fix the dressing 1102 to the intact skin surface for proper positioning over the wound 6.

The core 1108 can be placed on top of an optional mat 1106, which can be selected to cooperate with the wicking material layer 1104 in conveying fluid from the wound 6.

The core 1108 can distribute vacuum pressure differential to the surface contact layer 1104. The core 1108 is preferably collapsible and flexible and returns to its approximate original size and shape when vacuum pressure is removed. Without limitation, a suitable core material is an open-cell hydrophobic foam material which will maximize the above-listed desirable characteristics of the core 1108. This material can be integrated with the surface contact layer 1104. Other core materials may be used instead, such as hydrophilic foam, fiber matrix pads or a hybrid composite material comprising, e.g., beads and fibers.

The cover layer 1112 covers the other components including the compression core 1108 and the surface contact layer 1104. The cover layer 1112 is preferably relatively thin and flexible so that it can be collapsed over the underlying core 1108 to distribute the atmospheric pressure differential to all covered areas. Suitable, commercially-available, semi-permeable membrane materials are discussed above.

In an exemplary configuration, multiple top surface ports 1120*a,b* are provided on top of the cover layer 1112 and are connected to suitable fittings 1122 adapted for connecting to fluid-conveying tubing and conduits, which in turn connect to the equipment described below. Additional, perimeter ports 1124*a,b* are provided in the cover 1112 in proximity to the core perimeter and can be provided with tubular fittings 1126.

In operation the slip drains 1116 would adhere to the adhesive on the underside (contact surface) of the cover layer 1112 for extraction when the cover layer is removed, e.g., for a dressing change.

II. Closed-Wound Treatment Method with Dressing 1102

Figure 2:
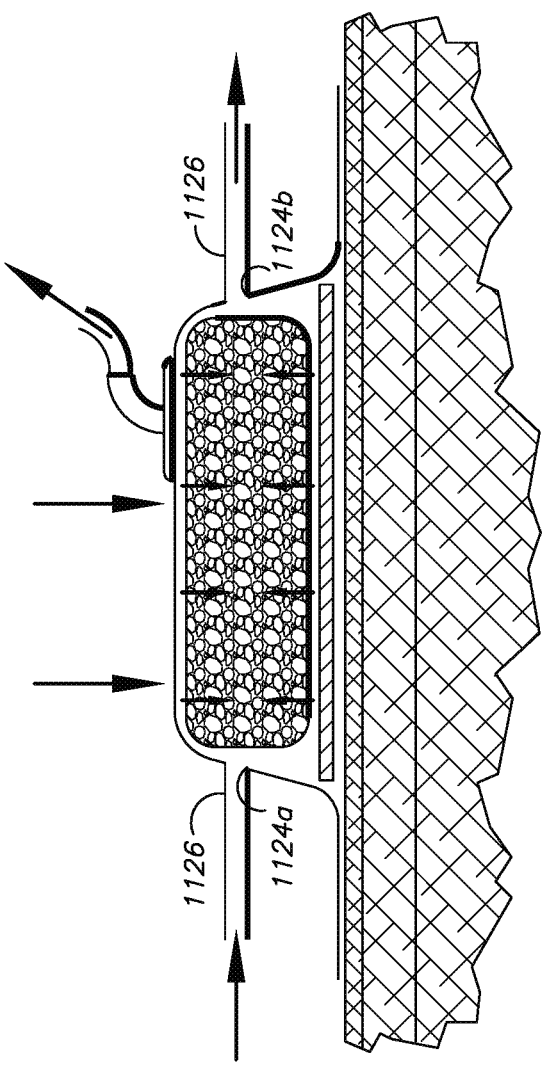
FIGS. 2-4 are cross-sections of the dressing system.
Figure 3:
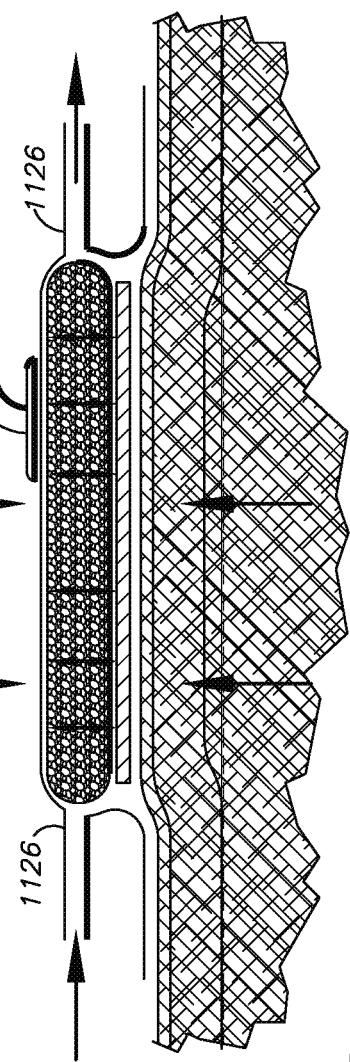
Figure 4:
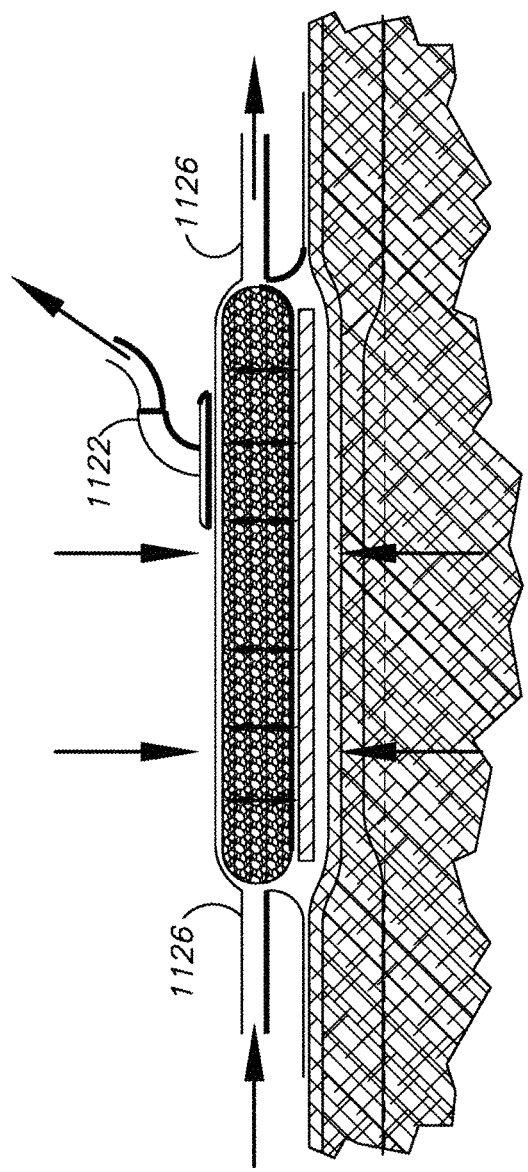

As shown in FIGS. 2-4, the dressing 1102 is generally adapted for use in a configuration providing internal compression and passive external resistance. More specifically and without limitation, the fluid forces and pressures generated and applied by the dressing 1102 can be described as follows:

1) The dressing 1102 exerts a downward (compression) force against the contact surface 42 to which it is applied, i.e., generally around the incision 6. The skin 42 and the tissue immediately beneath it are subject to an outwardly-directed lifting force due to the negative pressure in the dressing 1102. These forces and pressures tend to cancel whereby the dressing 1102 is in a compressed, balanced, equilibrium condition.

2) The dressing 1102 creates a pressure differential with respect to the surrounding ambient atmosphere and the dressing interior, exerting a compressive force corresponding to the ambient air pressure, which varies among different locations but tends to remain within certain well-known ambient air pressure ranges at given locations. The components within the dressing 1102 are compressed relative to each other.

3) Based on the balance of forces acting on the dressing 1102 in a steady state, a relatively fixed but flexible dressing 1102 tends to be firmly attached, i.e., molded, to the skin surface 42 by the operation of the atmospheric pressure differential.

4) The dressing 1102 converts the overlying intact skin 42 from an elastic layer to a relatively inelastic layer, which effectively resists pressure changes below the skin.

5) Pressure changes below the skin surface 42 are provided by the following physiologic functions: a) arterial pulsation, which tends to be amplified by the inelastic characteristic of the dressing 1102 coupled and cooperating with the skin 42; b) muscle contraction, which also tends to be amplified by this inelastic characteristic of the system; and c) the leakage of tissue fluid and the buildup of edema, e.g., intracellular edema.

Edema fluid buildup is the means by which leaking lymphatics are closed by compression. As pressure increases in the tissue from the buildup of edema fluid, the lymphatic vessels tend to be compressed. The dressing 1102 facilitates the earlier compression by amplifying the effects of bleeding and edema fluid buildup. Thus, the normal lymphatic system compression response, which can take approximately 3 days, can be significantly accelerated to the point that the edema phase is almost eliminated. Bacteria which appear over the several days of the normal edema phase are cleaned up in the wound site by macrophages and white cells which are also released into the wound over the several days. By eliminating the edema phase this entire inflammatory phase can also be eliminated. By achieving early reepithelialization, wound healing can be actually accelerated and the wound protected from bacterial invasion by this technique. Epithelial cells begin to move and migrate to the wound site based on the lymphatic system control. The edema formation and inflammation phases of normal wound healing can thus be avoided or at least minimized.

III. Alternative Embodiment External Dressing System 1130

Figure 5:
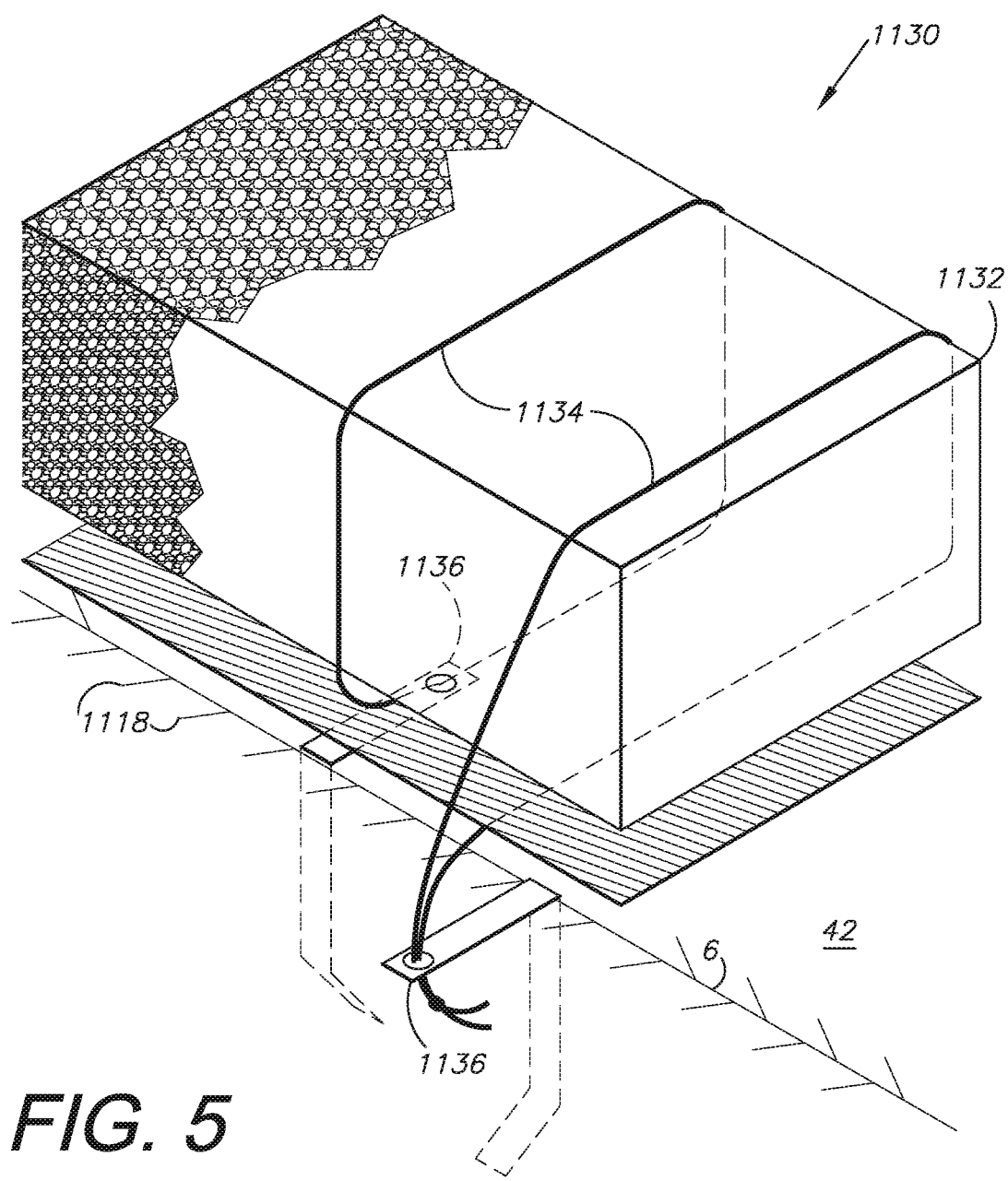
FIG. 5 is an isometric view of an alternative embodiment dressing system with sutures over a recoil core.

FIG. 5 shows an alternative embodiment external wound dressing 1130 with a core 1132, which can be encircled or otherwise in contact with sutures 1134, which are connected to the slip drains 1136.

IV. Alternative Embodiment External Dressing System 1140

Figure 6:
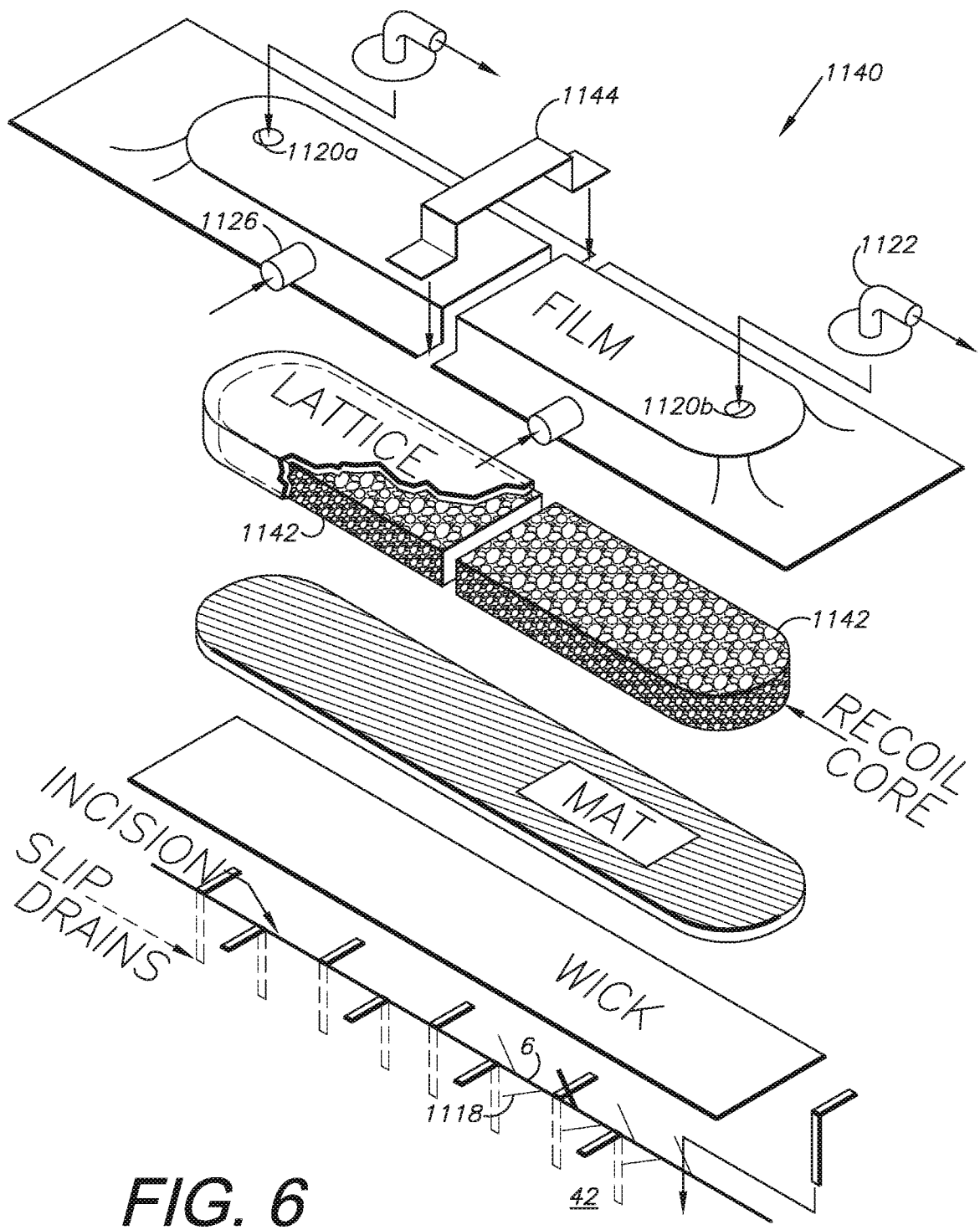
FIG. 6 is an exploded view of another alternative embodiment dressing system.

FIG. 6 shows another alternative embodiment external wound dressing 1140 with a pair of cores 1142 positioned in end-to-end relation. A film bridge 1144 covers abutting ends of the cores 1142.

It is to be understood that the invention can be embodied in various forms and is not to be limited to the examples discussed above. The range of components and configurations which can be utilized in the practice of the present invention is virtually unlimited.

Having thus described the disclosed subject matter, what is claimed as new and desired to be secured by Letters Patent is:

1. A dressing assembly for a wound or incision, which comprises:
    an external patient interface including an external fluid transfer component, said fluid transfer component being adapted for transferring fluid from the wound or incision;
    said external patient interface including an overdrape placed over said fluid transfer component in contact with a surrounding skin surface;
    said fluid transfer component including a porous core with a surface;
    said overdrape having an opening to said fluid transfer component;
    said opening forming a discharge port for discharging fluid from said dressing assembly;
    an internal fluid transfer component located in said wound or incision in fluidic communication with said external fluid transfer component and comprising multiple drain strips each having an internal portion located within said wound or incision and an external portion located externally thereto;
    said drain strips each comprising a flat, flexible material;
    each said drain strip external portion being folded over the skin surface adjacent to said wound or incision;
    a pressure source connected to said fluid transfer component;
    a wicking material cover enclosing said core and including a perimeter edge;
    said fluid transfer component having compressed and uncompressed configurations;
    said wicking material edge buckling and forming a laterally-projecting rim with said fluid transfer component in its compressed configuration;
    said core forming an air-entrapment interior zone with the application of negative pressure thereto;
    said core forming a fluid transfer zone at its outer surface and adjacent to said wicking material cover;
    said fluid transfer zone being adapted for directing fluid from said wound or incision to said discharge port;
    a sensor connected to said fluid transfer component and adapted for sensing a characteristic thereof and providing an output signal corresponding to said characteristic;
    a controller connected to said sensor and receiving input signals therefrom and providing an output signal to said pressure source; and
    a feedback loop connected to said controller output and to said controller for providing a feedback signal corresponding to said controller output and inputting same to said controller.

2. A method for treating a wound or incision externally, which comprises the steps of:
    locating a slip drain within said wound or incision;
    placing a wick over the closed wound or incision in contact with the slip drain;
    placing said external patient interface on a patient over the wound or incision;
    providing an overdrape and placing same over said fluid transfer component in contact with a surrounding skin surface;
    providing said fluid transfer component with a recoil core including a surface and a wicking material layer engaging same; and
    transferring fluid from the wound or incision to the fluid transfer component.

3. The method of claim 2, which includes additional step of providing said slip drain with an internal portion located within said wound or incision and an external portion located externally thereto.

4. The method of claim 3, which includes the additional steps of:
    providing a sensor connected to said fluid transfer component;
    sensing a characteristic thereof and providing an output signal corresponding to said characteristic;
    providing a controller connected to said sensor and receiving input signals therefrom;
    providing an output signal to said pressure source;
    providing a feedback loop connected to said controller output and to said controller; and
    said feedback loop providing an output signal corresponding to said controller output and inputting same to said controller in said feedback loop.

5. The method of claim 2, which includes additional step of providing said compression core with a fluid transfer zone.

6. The method of claim 2, which includes the additional steps of:
    providing a hemostasis treatment method; and
    applying a subdermal hemostatic pressure to said patient via said patient interface.

7. A surface-wound healing dressing for a closed wound or incision comprising:
    a slip drain configured for placement within said closed wound or incision;
    a wick configured for placement over said closed wound or incision and in contact with said slip drain;
    a mat configured for placement over said wick and configured for fluidic communication therewith;
    an external fluid transfer component including a foam recoil core and configured for placement over said mat;
    said external fluid transfer component having proximal and distal surfaces and a perimeter edge extending therebetween;
    an overdrape configured for placement over said external fluid transfer component in covering relation and configured for releasable attachment to a patient;
    wherein said dressing is configured for draining said closed wound or incision via said slip drain;
    wherein said recoil core is configured for compressing under negative pressure and recoiling to its original position when said negative pressure is removed;

a negative pressure source configured for extracting fluid and air from said dressing;

wherein said overdrape includes an opening to said external fluid transfer component distal surface forming a discharge port configured for discharging fluid from said dressing assembly; and wherein said overdrape includes perimeter ports to said external fluid transfer component perimeter edge.

8. The dressing assembly according to claim 7, wherein:
said perimeter ports comprise an inflow perimeter port and an outflow perimeter port;
said dressing assembly further comprising an input pump connected to said inflow perimeter port and configured for supplying fresh air to said dressing; and
said outflow perimeter port connected to said negative pressure source and configured for removing air from said dressing.

9. The dressing assembly according to claim 7, which includes:
an internal fluid transfer component located in said wound or incision in fluidic communication with said external fluid transfer component.

10. The dressing assembly according to claim 7, wherein:
said slip drain includes an internal portion configured for placement within said wound or incision and an external portion configured for placement externally thereto.

11. The dressing assembly according to claim 10, wherein:
said slip drain external portion is configured for folding over a skin surface adjacent to said wound or incision; and
said slip drain external portion being configured for attachment to said overdrape and for extraction when said overdrape is removed.

12. The dressing assembly according to claim 7, wherein:
said slip drain comprises a flat, flexible material.

13. The dressing assembly according to claim 7, wherein:
said slip drain comprises a plurality of slip drains.

14. The dressing assembly according to claim 7, wherein:
said wick comprises a proximal wicking material layer engaging said external fluid transfer component proximal surface and configured for overlying said wound or incision; and a distal wicking material layer engaging said external fluid transfer component distal surface and said overdrape.

15. The dressing assembly according to claim 7, wherein said recoil core comprises a reticulated, compressible foam material chosen from among the group consisting of polyurethane ether (PUE) and polyvinyl acetate (PVA).

16. The dressing assembly according to claim 7, wherein said wick comprises rayon.

17. The dressing assembly according to claim 7, wherein said negative pressure source comprises a manually-operated vacuum-type device.

18. The dressing assembly according to claim 7, which includes:
a wicking material cover enclosing said external fluid transfer component;
said cover including a perimeter edge;
said fluid transfer component having compressed and uncompressed configurations; and
said wicking material cover edge buckling and forming a laterally-projecting rim with said fluid transfer component in its compressed configuration.

19. The dressing assembly according to claim 18, which includes:
said recoil core forming an air-entrapment interior zone with the application of negative pressure thereto;
said recoil core forming a fluid transfer zone at its outer surface and adjacent to said wicking material cover; and
said fluid transfer zone being adapted for directing fluid from said wound or incision to said discharge port.

20. The dressing assembly according to claim 7, which includes:
a sensor connected to said fluid transfer component and adapted for sensing a characteristic thereof and providing an output signal corresponding to said characteristic;
a controller connected to said sensor and receiving input signals therefrom and providing an output signal to said pressure source; and
a feedback loop connected to said controller output and to said controller for providing a feedback signal corresponding to said controller output and inputting same to said controller.

\* \* \* \* \*